United States Patent [19]

Lukes et al.

[11] 3,976,705

[45] Aug. 24, 1976

[54] PREVENTION OF HYDROCHLORINATION

[75] Inventors: James J. Lukes, Cleveland; Norman L. Beckers, Chardon; Jack A. Borror, Chesterland, all of Ohio

[73] Assignee: Diamond Shamrock Corporation, Cleveland, Ohio

[22] Filed: June 25, 1969

[21] Appl. No.: 836,649

[52] U.S. Cl............................ 260/654 H; 260/654 S
[51] Int. Cl.²......................................... C07C 21/00
[58] Field of Search................................. 260/654 H

[56] References Cited
UNITED STATES PATENTS

| 2,799,716 | 7/1957 | Brummet | 260/654 |
| 3,061,652 | 10/1962 | Cayton et al. | 260/654 |

FOREIGN PATENTS OR APPLICATIONS

| 801,104 | 12/1968 | Canada | 260/648 |

OTHER PUBLICATIONS

Chemical Abstracts vol. 55 (1961) col. 9140d.

Primary Examiner—James O. Thomas, Jr.
Assistant Examiner—A. Siegel
Attorney, Agent, or Firm—William A. Skinner

[57] ABSTRACT

A method for preventing the undesired hydrochlorination of unsaturated hydrocarbons and chlorohydrocarbons in the presence of aluminum chloride involves the addition of a material capable of preferentially inactivating the ability of the $AlCl_3$ to catalyze hydrochlorination.

5 Claims, No Drawings

PREVENTION OF HYDROCHLORINATION

BACKGROUND OF THE INVENTION

It is well known to form unsaturated chlorinated hydrocarbons by the chlorination of hydrocarbons and partially-chlorinated hydrocarbons. Particularly it is well known to form lower molecular weight chlorinated hydrocarbons, e.g., perchloroethylene, by the vapor phase chlorination of hydrocarbons and chlorohydrocarbons of from 1–3 carbon atoms. For example, trichloroethylene and/or perchloroethylene may be prepared by the chlorination of ethylene dichloride in a fluid bed reactor using as the fluidizing medium various alumina-silica containing materials. Typically these materials comprise a major amount of silica and a minor amount of alumina. The products of this vapor phase chlorination, in addition to trichloroethylene and perchloroethylene, include a number of "light ends", i.e., chlorinated hydrocarbons boiling at a lower temperature than trichloroethylene or perchloroethylene, such as vinylidene chloride; "heavy ends", i.e., chlorinated hydrocarbons boiling at a higher temperature, such as hexachlorobutadiene; large amounts of hydrogen chloride, and small amounts of unreacted chlorine. The gaseous reaction products are then passed into a quench tower wherein the majority of the chlorinated hydrocarbons are converted to the liquid phase while anhydrous hydrogen chloride for the most part remains in the vapor phase and is readily separated. The liquid chlorinated hydrocarbons are then further treated, e.g., neutralized, scrubbed and dried, prior to separation into the desired end product components, trichloroethylene and/or perchloroethylene. This separation is generally accomplished by fractional distillation with the light ends often being recycled to the reactor for further reaction and the heavy ends either recycled for cooling or discarded.

While processes such as the foregoing are reasonably efficient and are in fact in commercial operation, there are certain problems which limit the efficiency and capacity of such plants. Thus, while it is desirable that the trichloroethylene and/or perchloroethylene obtained as final products be of the highest degree of purity possible, the attainment of high purity is complicated by the presence of a number of chlorinated components having boiling points close to the boiling points of trichloroethylene or perchloroethylene. Therefore, in order to obtain the desired purity, fractionating columns containing a large number of plates and operating under a heavy reflux are required. Since a significant portion of the capital investment of a chlorinated solvents plant lies in the cost of the fractionating columns, it would obviously be desirable to eliminate or reduce the formation of those chlorinated hydrocarbons having boiling points close to the boiling points of the intended products. For example, in the fractionation of perchloroethylene (b.p. 121°C.), unsymmetrical tetrachloroethane (U-tet, b.p. 129°C.) and 1,1,2-trichloroethane (b.p. 114°C.) are contaminants which are particularly difficult to remove. Thus, in general, in the production of unsaturated chlorinated hydrocarbons, it would be desirable to prevent the formation of saturated chlorinated hydrocarbons since fractionation would be facilitated and production would be increased (since the saturated hydrocarbons are generally produced by the hydrochlorination of the desired products).

It has now been found that the production of saturated chlorinated hydrocarbons, for example in a process such as described above involving the vapor phase chlorination of hydrocarbons and chlorohydrocarbons in the presence of an alumina-containing material, is caused by hydrochlorination, in the quench tower, of unsaturated hydrocarbons and chlorohydrocarbons, which hydrochlorination is catalyzed by aluminum chloride or active aluminum chloride complexes, generally formed in the reaction tower and carried over in the vapor phase with the gaseous reaction products.

STATEMENT OF THE INVENTION

Therefore it is an object of this invention to prevent the undesired hydrochlorination of unsaturated hydrocarbons and chlorohydrocarbons, said hydrochlorination being catalyzed by the presence of aluminum chloride.

It is a further object of the present invention to provide a method for obtaining unsaturated chlorinated hydrocarbons of a high degree of purity at an increased production rate by preventing the formation of saturated chlorinated hydrocarbons.

These and further objects and advantages of the present invention will become apparent to those skilled in the art from the specification and claims which follow.

As mentioned hereinabove, it has been discovered that the formation of saturated chlorinated hydrocarbons is often catalyzed by the presence of aluminum chloride. A method has now been found for preventing the hydrochlorination of unsaturated hydrocarbons and chlorohydrocarbons in the presence of aluminum chloride, which method comprises adding to said hydrocarbons and chlorohydrocarbons a compound capable of preferentially inactivating the ability of the aluminum chloride to catalyze hydrochlorination. The number of compounds capable of preferentially "poisoning" the aluminum chloride are many and they are so effective that the concentration of undesired saturated chlorinated hydrocarbons may be reduced to below detectable limits (50 parts per million).

DESCRIPTION OF THE PREFERRED EMBODIMENTS

While the invention in general is applicable to the prevention of the aluminum chloride-catalyzed hydrochlorination of any unsaturated hydrocarbon or chlorohydrocarbon, it finds special use in the prevention of the liquid phase, aluminum chloride-catalyzed, hydrochlorination of unsaturated, at least partially-chlorinated, hydrocarbons; said liquid phase resulting from the quenching of the gaseous reaction products of the vapor phase chlorination, in the presence of an aluminum-containing material, of hydrocarbons and partially-chlorinated hydrocarbons. Quenching will be understood to refer to the liquefaction of the majority of the gaseous chlorinated hydrocarbons while maintaining the anhydrous HCl in the vapor phase, i.e., anhydrous quenching. Therefore, means other than a quench tower, wherein the gaseous reaction products are contacted with a liquid body of chlorinated hydrocarbons, are to be considered equivalent, e.g., condensers. While useful in the production of other unsaturated chlorinated hydrocarbons, for the sake of clarity and in view of their commercial significance, the invention will be described by reference to a process, as described hereinabove, for the production of trichloroethylene and/or perchloroethylene. Likewise, while the invention will be described primarily with respect to the prevention of the formation of unsymmetrical tetrachloroethane, it is equally applicable to the prevention of the formation of other saturated chlorinated hydrocarbons, e.g., 1,1,2-trichloroethane from the hydrochlorination of dichloroethylene.

Specifically then, the present invention involves the addition to the quench tower of a material capable of preferentially inactivating the ability of the $AlCl_3$ present to catalyze hydrochlorination. This may be readily accomplished by merely injecting a small amount of said compound directly into the liquid phase. The amount of compound introduced is generally equivalent, on a molar basis, to the quantity of aluminum chloride present in the liquid phase. Smaller than equimolar amounts may be used but such amounts generally result in a reduction in the effectiveness of the poisoning of the catalyst. While, in practice, larger amounts of the compound may be introduced to facilitate control under varying reaction conditions, substantially no other purpose is served by using greater than equimolar amounts.

A surprisingly wide variety of compounds have been found to be effective for poisoning the aluminum chloride catalyst, that is, for preferentially inactivating the ability of the $AlCl_3$ to catalyze hydrochlorination. Illustrative of such compounds, or "poisons", are: water; alcohols, such as methanol and ethanol; organic acids, such as acetic acid; aldehydes, such as acetaldehyde; nitro-organics, such as 2-nitropropane; ketones, such as acetone; alkoxides, such as sodium methoxide; ammonia and hydrazine. Also useful are such classes of compounds as amines, amides, nitriles, thiols, sulfonic acids, anilines, phenols, esters, glycols, acetals, etc. In general, any compound, or mixture of compounds, capable of preferentially inactivating the ability of the $AlCl_3$ to catalyze hydrochlorination may be used. In a process for the production of trichloroethylene and perchloroethylene involving an aqueous alkali neutralization step, it is particularly preferred, although not essential, that the additive compound be water-soluble in order that it may be removed with the aqueous phase following the neutralizing operation. However, especially in processes where removal of the acidic materials is by non-aqueous techniques, e.g., thermal stripping, compounds which may be considered "heavy ends" are also useful since they can be separated during subsequent fractionation.

It is thought to be surprising that water operates as effectively as a catalyst poison in this reaction as it does, since it is generally known that the presence of even trace amounts of water in a system containing substantial quantities of anhydrous HCl is to be avoided or severe corrosion can be expected. However, with careful operation, no corrosion is in fact noticed. Despite this surprising finding, water is not generally the preferred compound of the present invention since it does lead to other side effects which can be undesirable in certain systems. For instance, when the material used in the reactor contains, in addition to alumina, a large proportion of silica, it is to be expected that a portion of the silica will volatilize as silicon tetrachloride and be carried into the liquid in the quench tower along with the aluminum chloride. While this silicon tetrachloride does not have a catalytic effect on the hydrochlorination reaction, and hence, generally causes no problem, silicone tetrachloride, in the presence of water, is at least partially converted to amorphous silica which tends to accumulate on the quench tower walls and plug the various entrance and exit lines. Thus, when silica is present in the reactor, those catalyst poisons which do not precipitate insoluble silica in the quench tower, notably alcohols, are preferred. Experiments indicate that the mechanism of catalyst poisoning is that of the reaction between the aluminum chloride and the alcohol to form an aluminum alcoholate, rather than hydrochlorination of the alcohol to an alkyl chloride with the consequent liberation of water, which water in turn poisons the catalyst.

That the process of the present invention offers a significant improvement in methods for the production of unsaturated, chlorinated hydrocarbons is apparent from the many advantages obtained, some of which are as follow.

The most immediate advantage of the process of the present invention, as it applies to the production of perchloroethylene, lies in the dramatic increase in production that may be realized. For example, in a plant having fractionating columns incapable of producing more than 125 tons/day of perchloroethylene if the U-tet concentration is to be kept below 2000 ppm, 200 tons/day of a product containing less than 50 ppm U-tet is readily produced after the addition of methanol in amounts approximately equivalent to the $AlCl_3$ content of the quench tower liquid. From this it will be readily apparent that, in the design of a new plant for the production of perchloroethylene, a considerable savings in capital investment could be realized, without a reduction in design capacity. This is due to the fact that a substantial portion of the cost of a plant resides in the cost of fractionating columns and the fractionating requirements will be substantially reduced by the process of the present invention.

Another significant advantage lies in the substantially reduced steam requirements which accrue from the fact that a heavy reflux of the liquid being fractionated is not needed in order to obtain good separation.

A further advantage of the present invention, again described in relation to its application to the production of perchloroethylene by a process as outlined above, resides in the greater freedom of choice of the fluid bed medium used in the reactor. Thus, since it may be demonstrated that the quantity of U-tet produced in the quench tower by the hydrochlorination of trichloroethylene in the presence of aluminum chloride is related to the quantity of alumina present in the fluid bed medium in the reactor, it will be obvious that one method for reducing the quantity of U-tet produced would be to use a fluid bed medium having a low alumina content. However, this is impractical for a number of reasons. In the first place, low alumina (13–15%) materials of the type usually used are not readily available and hence demand a premium price. Furthermore, it has been found that a reduction in the alumina content of the fluid bed medium results in a change in the production distribution and particularly results in the formation of an increased proportion of undesirable heavy ends. Thus, a process such as the present invention, which allows the use of more readily available high alumina (30%) materials, results in considerable economies while still allowing efficient and, in fact improved, operation.

In order that those skilled in the art may more readily understand the present invention and certain specific embodiments by which it may be carried into effect, the following specific examples are afforded.

In each of the following examples, unless otherwise noted, a closed vessel equipped with stirring means is used. The reaction mixture ("quenched solvent") consists of 600 grams of perchloroethylene and 400 grams of trichloroethylene. During the course of each test the temperature of the mixture is maintained at 66°C., ± 5°C., and the solvent is continuously sparged with a stream of anhydrous HCl.

EXAMPLE 1

The reaction mixture is brought to temperature and 820 ppm $AlCl_3$ is added. After 20 minutes, the concentration of U-tet is 0.86 percent by weight. After 35 minutes, this concentration rises to 2.55 percent. At this time 100 ppm of water is added. Fifteen minutes after the addition of the water the U-tet concentration is determined to be 2.45 percent, thus indicating that the hydrochlorination reaction is successfully halted.

EXAMPLE 2

In a first reaction vessel there is placed 0.012 mole of $AlCl_3$. After 40 minutes of reaction, the U-tet concentration is determined to be 2.97 percent. In a second reaction vessel there is also placed 0.012 mole of $AlCl_3$ together with 0.012 mole of acetic acid. After 40 minutes of reaction, the U-tet concentration is found to be only 0.1 percent by weight.

EXAMPLE 3

Into a reaction vessel are placed 0.009 mole of $AlCl_3$ and 0.007 mole of acetaldehyde. After 25 minutes, only 0.06 percent of U-tet is found.

EXAMPLE 4

Into a reaction vessel are placed 0.012 mole of $AlCl_3$ and 0.012 mole of 2-nitropropane. After 1 hour of reaction only 0.036 percent U-tet is found.

EXAMPLE 5

Into a reaction vessel is placed 0.012 mole of $AlCl_3$. After reaction for 20 minutes, a U-tet concentration of 4.26 percent is found. Shortly after this determination, 0.012 mole of acetone is added and 40 minutes later the U-tet concentration is only 4.51 percent.

EXAMPLE 6

Reaction is commenced in the presence of 0.012 mole of $AlCl_3$. After 20-25 minutes, 0.012 mole of anhydrous ammonia is added and the U-tet concentration at this time is determined to be 4.98 percent by weight. Ninety minutes later the U-tet concentration is only 5.08 percent.

EXAMPLE 7

After 45 minutes of reaction in a vessel containing 0.012 mole each of $AlCl_3$ and hydrazine, there is found only 0.08 percent U-tet.

EXAMPLE 8

Into a reaction vessel as in the preceding examples but containing 405 grams of trichloroethylene and 365 grams of perchloroethylene, and already containing 0.044 percent U-tet, are placed 0.0051 mole of $AlCl_3$ and 0.0034 mole of ethyl alcohol. Reaction is begun and continued for an hour. Despite the addition of another 0.0014 mole of $AlCl_3$ after approximately 30 minutes, the total concentration of U-tet rises to only 0.06 percent.

While the invention has been described with reference to certain specific and preferred embodiments thereof, it is not to be so limited since changes and alterations may be made therein which are within the scope of the appended claims.

We claim:

1. In a process for the production of trichloroethylene and perchloroethylene by the vapor phase chlorination of ethylene and chlorinated ethanes and ethylenes in the presence of an alumina-containing fluid bed medium and involving the step of anhydrously quenching the gaseous reaction products from said vapor phase chlorination, the improvement which comprises preventing the undesired, aluminum chloride-catalyzed hydrochlorination of unsaturated, chlorinated ethylenes by the addition to the quenched reaction products of at least one compound capable of preferentially inactivating the ability of aluminum chloride to catalyze hydrochlorination.

2. A process as in claim 1 wherein the compound capable of inactivating the aluminum chloride is added in amounts approximately equal, on a molar basis, to the amount of aluminum chloride present.

3. A process as in claim 1 wherein the compound capable of inactivating the aluminum chloride is selected from the group consisting of water, alcohols, carboxylic acids, ketones, aldehydes, nitro-organics, ammonia and hydrazine.

4. A process as in claim 1 wherein the compound capable of inactivating the aluminum chloride is alcohol.

5. An improvement in the process for the production of trichloroethylene and/or perchloroethylene by the vapor phase chlorination of ethylene and chlorinated ethanes and ethylenes in the presence of an alumina-containing fluid bed medium and including the step of anhydrously quenching the gaseous reaction products from said vapor phase chlorination, which improvement consists essentially of preventing the undesired, aluminum chloride-catalyzed hydrochlorination of unsaturated, chlorinated ethylenes by the addition to the quenched reaction products, in amounts approximately equimolar to the $AlCl_3$ present, of a compound selected from the group consisting of water, ethanol, methanol, acetic acid, acetaldehyde, 2-nitropropane, acetone, sodium methoxide, ammonia and hydrazine.

* * * * *